United States Patent [19]
Fukuda et al.

[11] Patent Number: 5,328,843
[45] Date of Patent: Jul. 12, 1994

[54] METHOD FOR ALLOCATING CELLS AND CELL ALLOCATION DEVICE

[75] Inventors: Jun Fukuda, 1-7-409, Hiroo-4-chome, Shibuya-ku, Tokyo; Hideo Kawaguchi; Takejiro Ushiroda, both of Saitama; Norio Shimizu, Sayama; Kazuo Sato, Tokyo, all of Japan

[73] Assignees: Hitachi, Ltd.; Jun Fukuda, Tokyo, Japan

[21] Appl. No.: 660,875

[22] Filed: Feb. 26, 1991

[30] Foreign Application Priority Data

Feb. 27, 1990 [JP] Japan .................................. 2-44560

[51] Int. Cl.$^5$ .......................... C12N 5/06; C12M 3/00
[52] U.S. Cl. ...................... 435/240.23; 435/240.243; 435/284; 435/287; 435/291
[58] Field of Search ............. 435/29, 30, 173, 240.23, 435/240.241, 240.243, 284, 285, 291, 292, 293, 297, 298, 299–301, 310, 809, 810, 287; 422/100, 102, 104; 427/4, 240, 272, 282; 118/400, 401, 406, 407, 412, 504; 101/127, 123, 124, 115; 204/153.12, 403

[56] References Cited

U.S. PATENT DOCUMENTS

| | | | |
|---|---|---|---|
| 3,745,091 | 7/1973 | McCormick | 435/301 |
| 3,883,398 | 5/1975 | Ono | 435/301 |
| 4,258,135 | 3/1981 | Meunier | 435/301 |
| 4,323,536 | 4/1982 | Columbus | 422/100 |
| 4,549,952 | 10/1985 | Columbus | 422/100 |
| 4,612,873 | 9/1986 | Eberle | 118/411 |
| 4,834,946 | 5/1989 | Levin | 435/293 |
| 4,853,188 | 8/1989 | Toya | 422/102 |
| 4,894,343 | 1/1990 | Tanaka et al. | 435/301 |
| 5,108,926 | 4/1992 | Klebe | 435/292 |

FOREIGN PATENT DOCUMENTS

| | | | |
|---|---|---|---|
| 3732142 | 4/1989 | Fed. Rep. of Germany | 435/284 |
| 1141588 | 6/1989 | Japan | 435/284 |
| 2084174 | 3/1990 | Japan | 435/284 |

OTHER PUBLICATIONS

Proceedings of National Academy of Science, USA, vol. 74, No. 10, pp. 4516–4519 (Oct. 1977).
Science, vol. 244, 1989, 585–587 (May 1989).

Primary Examiner—Michael G. Wityshyn
Assistant Examiner—William H Beisner
Attorney, Agent, or Firm—Fay, Sharpe, Beall, Fagan, Minnich & McKee

[57] ABSTRACT

Apertures in a definite shape having a definite width and length are provided on one surface of a plate material having a definite thickness. One end of the apertures is connected with the other surface of the plate material and at the same time, is opened. Another end of the apertures is connected with the plate material on one surface and is also opened toward the other surface of a culture substrate. The plate material is closely contacted to one surface of the culture substrate for allocating nerve cells and observing growth of the neurites. Then, the cell suspension is supplied to the apertures. The cells in the suspension are allocated on the culture substrate in response to the apertures by centrifugation or spontaneous sedimentation. The plate material is then withdrawn.

48 Claims, 15 Drawing Sheets

F I G. 10
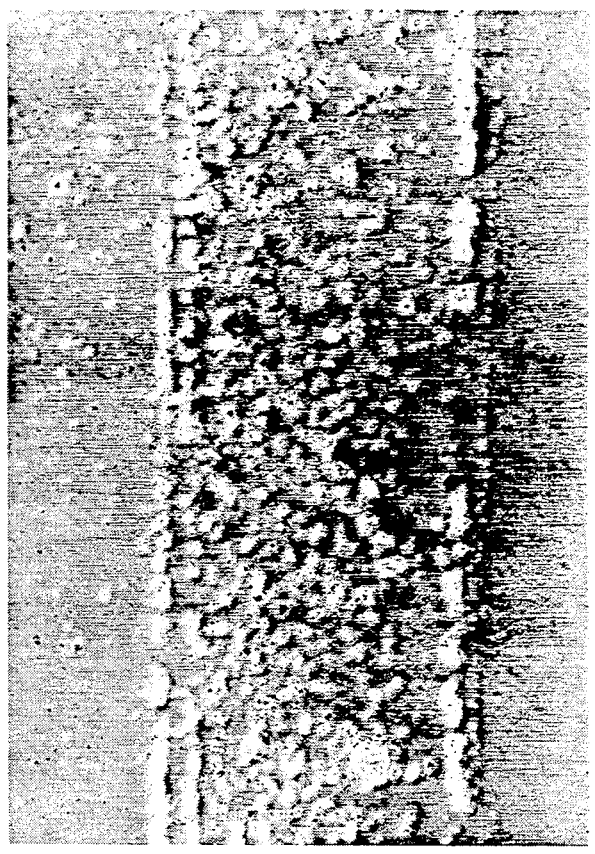
500μm
F I G. 11
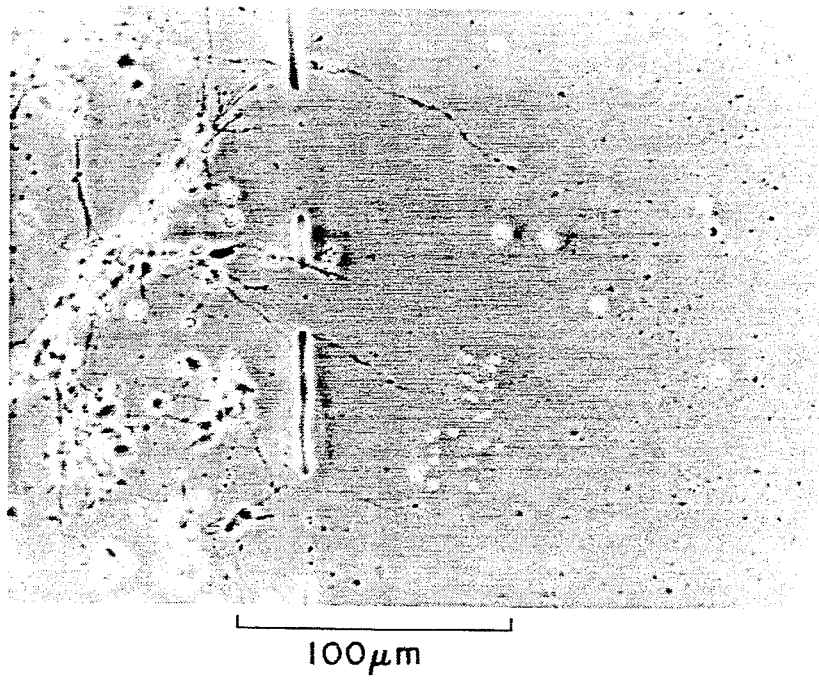
100μm

F I G. 12
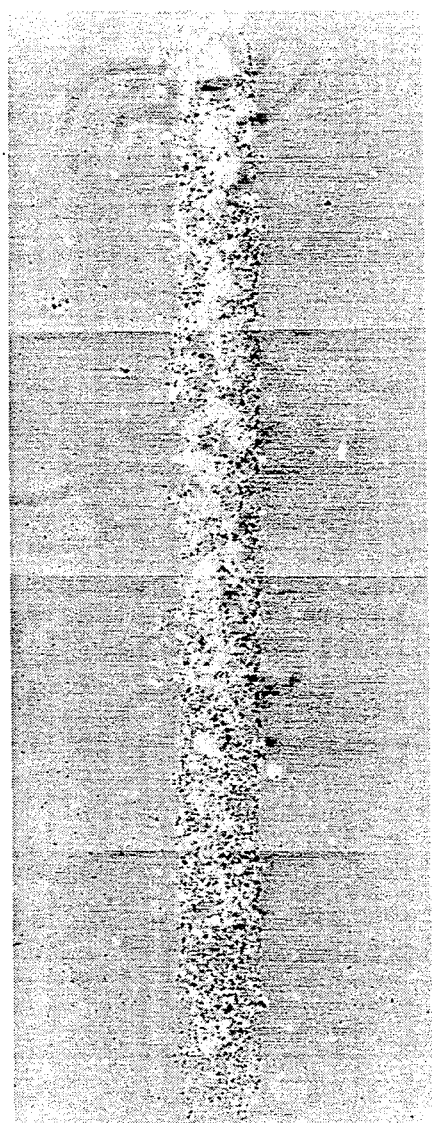
200μm

F I G. 13
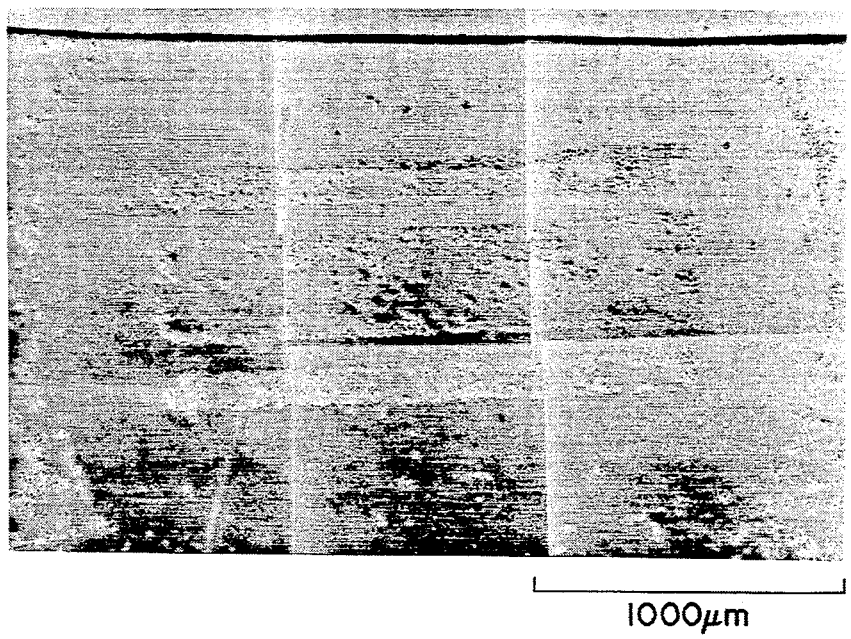

F I G. 14
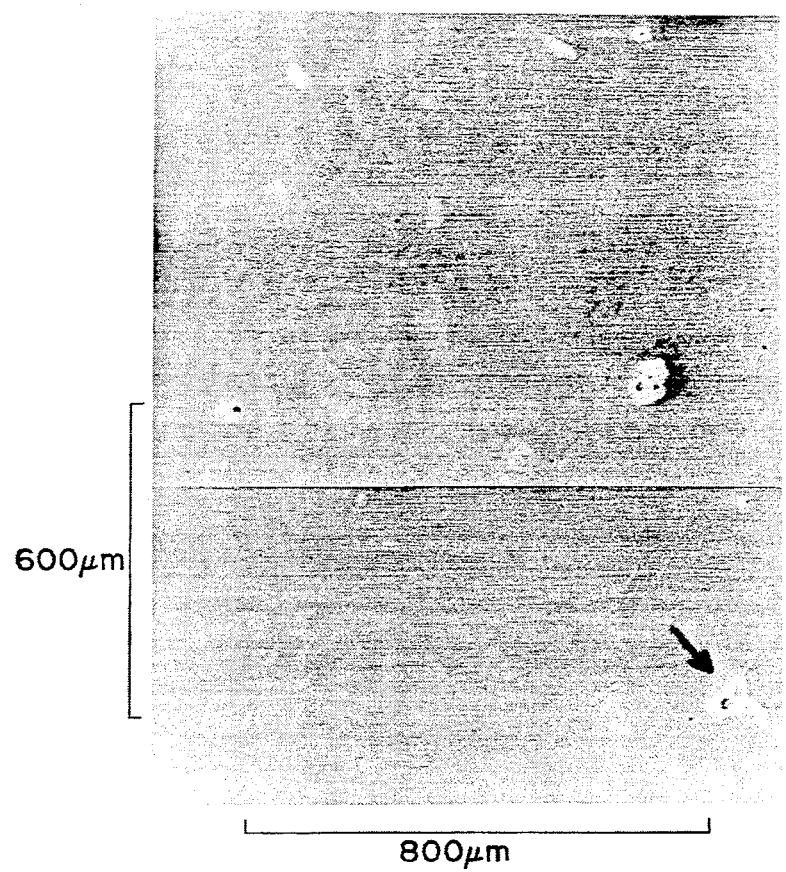
600μm
800μm
F I G. 15
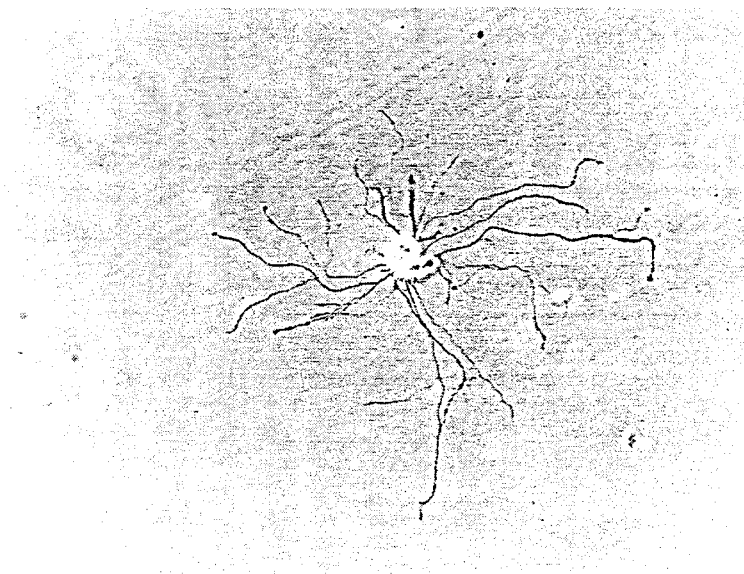

500μm

500μm

F I G. 18
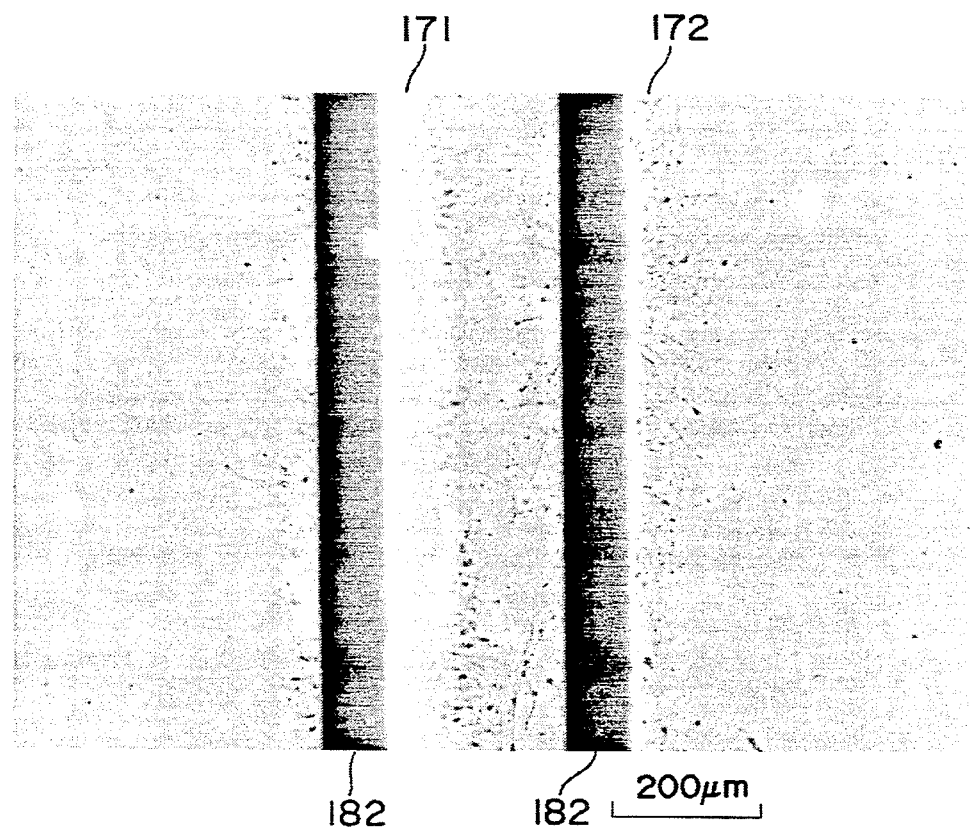

METHOD FOR ALLOCATING CELLS AND CELL ALLOCATION DEVICE

BACKGROUND OF THE INVENTION

1. Field of the Invention

The present invention relates to a method for artificially allocating (arranging or orienting) cells, at a specific zone on the surface of a substrate, which express their functions by such allocating, for example, cells in the nervous system, liver, kidney, etc., thereby to reconstruct an in vivo order outside the living body, i.e., in vitro, and a device therefor. The present invention also relates to a method for inputting and outputting in vitro the functions expressed by the cells allocated by the method for allocating and then cultured and an apparatus therefor.

2. Description of the Related Art

In recent years, it has been made possible to culture cells in the nervous system, liver, kidney, etc. in a dissociated state in vitro, due to the progress of cell culture techniques. However, these cells express their function in their order. For example, neurons are connected with each other in vital tissues to form circuits, whereby the function of information processing is expressed. Accordingly, if these cells are allocated and cultured in vitro, it would be possible to artificially prepare biological devices having various functions.

In order to make the cells in these tissues dissociate in vitro for incubation of these cells, however, the cell order possessed in the tissues is destroyed. As the result, a problem occurs that their functions are lost, although it is possible to culture the cells.

On the other hand, it is possible to culture cells without disconnecting the cells as they are in the tissues withdrawn from the living body. However, the respective cells in the tissues cannot be identified. After all, it has been difficult to express the function desired to be utilized. For example, while it has been wished to utilize input and output signals at a specific neural circuit in the nerve tissue, the neurons for constructing the neural circuit could not be specified so that it has been impossible to utilize the desired input and output signals.

As one method for allocating specific cells once dissociated on the surface of the same culture substrate and reconstructing the allocating in order to eliminate problems, a machine for sorting cells one by one comprising a combination of a cell sorter and an apparatus for stepping operation of a culture dish has been provided for practical use. However, the machine requires as many repetitions of the sorting operation as the number of the cells to be sorted. In addition, when one cell was plated on the surface of the culture substrate, the next cell would then be put on the surface of the culture substrate so that it was difficult to arrange many cells rapidly in a simple manner.

Another method comprises providing a multicompartment chamber on a culture substrate having narrow grooves on its surface, introducing a suspension of neurons via one chamber, precipitating and adhering the cells onto the culture substrate at a specific position, and culturing the culture substrate to perform elongation of neurites via the groove (Proc. Natl. Acad. Sci. USA, Vol. 74, No. 10, pp. 4516-4519, 1977 and Science, Vol. 244, pp. 585-587, 1989). According to this method, however, there is a danger that the multicompartment chamber might inhibit physically and biologically the elongation of neurites and expression of the functions.

The method involves an additional drawback that interaction of the cells cannot be observed upon incubation so that the relationship between cells connected with each other cannot be specified.

Furthermore, in order to reconstruct the order of cells in vivo and utilize their functions, the system should be kept sterile and needless to say, the cells should not be damaged. Simple operation makes maintenance of sterility easy and rapid processing results in no damage of the cell activity during the processing. From a practical viewpoint, these are important factors which should not be underrated.

SUMMARY OF THE INVENTION

The present invention has been made in view of the foregoing actual situation. An object of the present invention is to provide a practical method and device for allocating the once dissociated cells on a culture substrate rapidly in a simple manner to reconstruct the in vivo order and at the same time, to utilize the functions possessed by the cells.

As a result of extensive investigations to solve the foregoing problems, the present inventors have newly developed a method for allocating cells in a cell suspension onto the surface of a culture substrate at a specific zone and a device for cell allocating applied to the method. The present invention has thus come to be accomplished.

That is, the present invention provides a method for allocating cells on a culture substrate at a specific zone which comprises:

introducing a cell suspension into a cell allocation device which is mounted to a culture substrate and divides a specific zone on the surface of the culture substrate, depositing and adhering the cells in the cell suspension on the surface of the culture substrate, and then withdrawing the cell allocation device from the surface of the culture substrate.

The cells in the cell suspension are precipitated on and adhered to the surface of the culture substrate due to spontaneous sedimentation, or precipitated on and adhered to the surface of the culture substrate by a centrifuging operation.

The present invention also provides a device comprising:

a culture substrate, on the surface of which a conductive material is placed at a specific zone of the allocated cells, for example, so as to independently contact each of two cells independently allocated, and electrical signals can be input or output via the conductive material, whereby response of the allocated cells per se or axons elongated from the cells to electrical signals can also be observed.

BRIEF DESCRIPTION OF THE DRAWINGS

FIG. 10 is a picture showing the state of the cells allocated on the surface of the culture substrate according to the embodiment shown in FIG. 1, two hours after initiation of the culture;

FIG. 11 is a picture showing the state of the cells allocated on the surface of the culture substrate according to the embodiment shown in FIG. 1, 24 hours after initiation of the culture;

FIG. 12 is a picture showing the state of the cells allocated on the surface of the culture substrate according to the embodiment shown in FIG. 2, 56 hours after initiation of the culture;

FIG. 13 is a picture showing the state of the cells allocated on the surface of the culture substrate according to the embodiment shown in FIG. 3, two hours after initiation of the culture;

FIG. 14 is a picture showing the state of the cells allocated on the surface of the culture substrate according to the embodiment shown in FIG. 4, two hours after initiation of the culture;

FIG. 15 is a picture showing the state of the cells allocated on the surface of the culture substrate according to the embodiment shown in FIG. 4, 18 hours after initiation of the culture;

FIG. 18 is a picture showing the state of the cells allocated on platinum electrodes at the surface of the culture substrate according to the embodiment shown in FIG. 9, 70 hours after initiation of the culture.

DESCRIPTION OF THE PREFERRED EMBODIMENTS

Figure 1A:
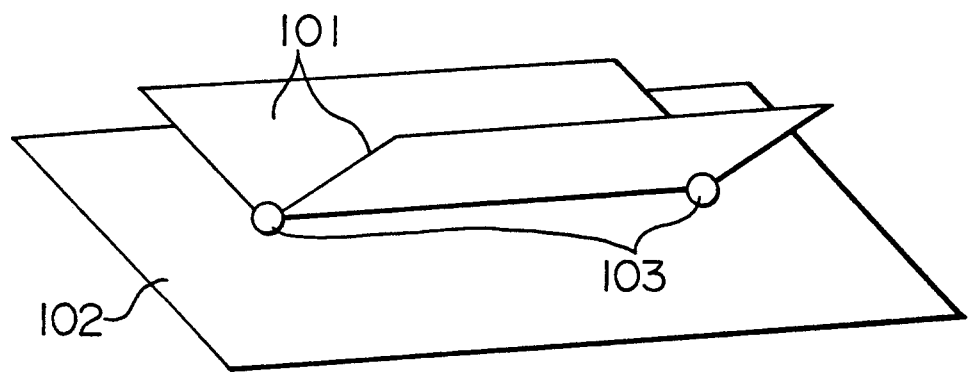
FIGS. 1A and 1B are a perspective view and a plan view, respectively, explaining the method for allocating cells according to the present invention.

The method of the present invention comprises mounting a cell allocation device onto a culture substrate so as to provide a specific zone on the surface of the culture substrate on which the cells are to be allocated, and allocating the cells in a cell suspension on the surface of the culture substrate at a specific zone thereof by the cell allocation device. According to the method, the cells are deposited and adhered on the surface of the culture substrate, and the cell allocation device is then withdrawn from the surface of the culture substrate.

The cells allocated in the present invention may be those of a single kind or different cells of at least two kinds but are not particularly restricted. In particular, by allocating different cells of at least two kinds onto the surface of the same culture substrate at different zones thereof, it becomes possible to exhibit various useful functions. Where two or more different cells are allocated, the allocating operation may be sequentially performed for every kind of cell, using the cell allocation device composed of a single compartment. However, when the cell allocation device having multiple compartments which are independent from each other and having cell feeding portions corresponding to the compartments is used and the allocating operation is performed by feeding different cell suspensions into the respective cell feeding portions, different cells of multiple kinds can be rapidly allocated independently on the surface of the same culture substrate at different zones thereof, in a simple manner.

In the present invention, the cells allocated by the cell allocation device are precipitated and plated onto the surface of the culture substrate by spontaneous sedimentation due to gravity or by sedimentation by a centrifugal force. In the case of spontaneous sedimentation, damage to the cells is extremely minimized and the probability of their cells migrating out of the specific zones on the surface of the culture substrate is extremely low. In addition, due to reduced steps of the allocating operation, it is easy to maintain sterility of the system.

In particular, the method is effective for independently allocating different cells of plural kinds on the surface of the same culture substrate at different zones thereof. Further, in the case of sedimentation due to a centrifugal force, it is advantageous in that the cells can be precipitated and plated onto the surface of the culture substrate extremely rapidly. This embodiment is particularly effective for rapidly collecting the suspended cells in large quantities onto the surface of the culture substrate, when a cell density of the cell suspension can be rendered high only with difficulty.

Where the cells are precipitated and plated onto the surface of the culture substrate by spontaneous sedimentation in the present invention, it is necessary that the cell allocation device be maintained on the surface of the culture substrate, until substantially all the cells held in the cell allocation device are precipitated and plated onto the surface of the culture substrate. However, a the time period during which the cells are kept in the cell allocation device is required to be within such a range that the activity of the cells is not damaged. The limit to the time period during which cell activity is not damaged is not particularly determined since the time period varies depending on kind of cells, but for neurons in the retina or optic tectum of a chick embryo, the limit is a few hours.

Herein, the time period until substantially all the cells held in the cell allocation device are precipitated and plated onto the surface of the culture substrate depends on the shape and material of the cell allocation device, the property of the cells and the properties of the medium in which the cells are suspended. Therefore, the shape of the cell allocation device should be determined taking into account the materials and properties described above.

On the other hand, in the case that the cells are precipitated and plated onto the surface of the culture substrate by a centrifugal force in the present invention, conditions for the centrifugal force should be chosen from such mild conditions that do not damage the cells. For example, in neurons in the retina or optic tectum of a chick embryo, the centrifugal force may be applied for 3 minutes under conditions of 500 to 1200 rpm.

The cell allocation device used in the method of the present invention is desirably polished so precisely as to closely contact with the surface of the culture substrate, so that cells having a diameter of about several tens of $\mu$m do not substantially invade into the other zones on the surface of the culture substrate upon the allocating operation. In particular, when the cells are precipitated and plated onto the surface of the culture substrate using a centrifugal force, it is essentially required that the cell allocation device be precisely polished sufficiently so that the cells do not invade out of the specific zone to be allocated by the centrifugal force.

After the allocating treatment of the cells, the cell allocation device of the present invention is withdrawn from the surface of the culture substrate. This is necessary to avoid the possibility that the cell allocation device might interfere growth of the cells and expression of the functions physically or biologically and to make it possible to observe the interaction of the cells and specify connections of the cells upon incubation.

After withdrawal of the cell allocation device, the culture substrate on which the cells have been allocated at a specific zone is subjected to the step of incubation. In the step of incubation, for example, where neurons of multiple kinds are allocated on the surface of the culture substrate, nerve cells are extended from the neurites to form synapses thereby to connect with each other. Thus, a neural circuit is constructed.

Further, in the method of the present invention, it is possible to control cell density on the surface of the culture substrate at a specific zone thereof by changing the quantity and/or concentration of the cell suspension introduced. By choosing an appropriate quantity and/or concentration of the cell suspension, the cells may also be allocated in a single layer at the specific zone described above.

Any materials may be used as those for the cell allocation device and culture substrate used in the method of the present invention, unless they inhibit growth of the cells and expression of the functions. Examples of the materials for the cell allocation device include silicon, plastic, glass, etc. and examples of those for the culture substrate are glass, plastic and silicon, and those obtained by coating cell-adhesive polypeptide, protein, etc. on the surface of the former three materials.

As one example for externally observing the functions of the cells allocated and cultured on the surface of the culture substrate according to the present invention, there is used a culture substrate, containing electrodes, which is designed to contact a conductive material with the cells allocated on the surface of the culture substrate. Electrical signals can thus be input and output between the conductive material and the cells via the. That is, electrodes for the conductive material are previously patterned on the surface of the culture substrate in the shape of the specific zone divided by the cell allocation device, and this culture substrate is used in combination with the cell allocation device. When it is difficult to place the cell allocation device strictly at a definite position, the pattern of conductive material previously patterned on the surface of the culture substrate is desirably designed to leave a relatively certain margin.

Any materials can be used for the conductive material unless they inhibit growth of the cells and expression of the functions. Examples of the materials include platinum, gold, silicon and conductive plastic, and those obtained by coating cell-adhesive polypeptide or protein on the surface of such materials. For patterning these conductive materials on the surface of the culture substrate, it is advantageous to use technology for preparing semiconductors. In the electrodes prepared by thickly coating cell-adhesive polypeptide or protein on the surface of a material, etc., the polypeptide or protein plays a role as a capacitor and therefore, changes in electrical signals of the cells can be output.

Firstly, an embodiment of the cell allocation device of the first type according to the present invention is described below.

Figure 1B:
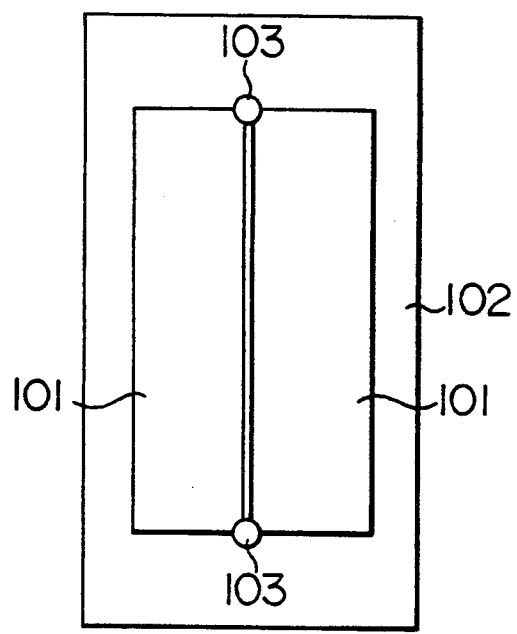

FIGS. 1A and 1B are a perspective view and a plan view, respectively, explaining the method for allocation of the present invention. Cell allocation device 101 is temporarily fixed on the surface of culture substrate 102 with dental utility wax 103. By two detachable plates 101 temporarily fixed on the surface of the culture substrate 102, the surface of the culture substrate 102 is divided into a first zone as described above and a second zone different from the first zone. A cell suspension is dropped onto any one or both surfaces of the plates 101. Then, a centrifugal force is applied to the cell suspension using an apparatus designed to impart an appropriate centrifugal force and the cells are precipitated and plated at the first zone between the cell allocation device plates 101.

Materials for plates 101 are not particularly limited but any material may be used unless it inhibits growth of the cells and expression of the functions. As such materials, there may be used, for example, glass, plastic and the like. Materials for fixing the plates 101 are not particularly limited, either, and any material may be used unless it inhibits growth of the cells and expression of the functions. Materials for the culture substrate 102 are not particularly limited but any material may be used so long as it does not inhibit growth of the cells and expression of the functions. As such materials, there may be used, for example, plastic, or glass coated with collagen, poly-L-lysine, and the like.

Figure 2A:
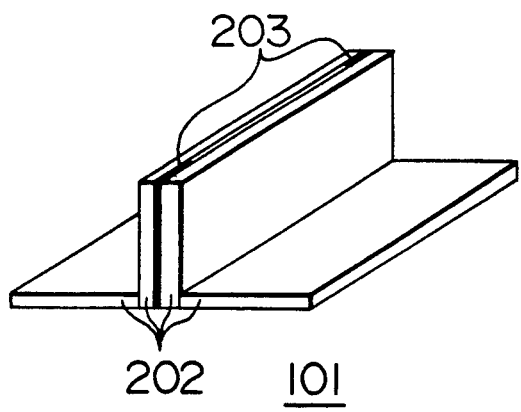
FIGS. 2A, 2B and 2C are a perspective view and a plan view, which show an embodiment of the cell allocation device of first type in accordance with the present invention, explaining the method for allocating cells according to the present invention; and a plan view of a modification of the embodiment, respectively.
Figure 2B:
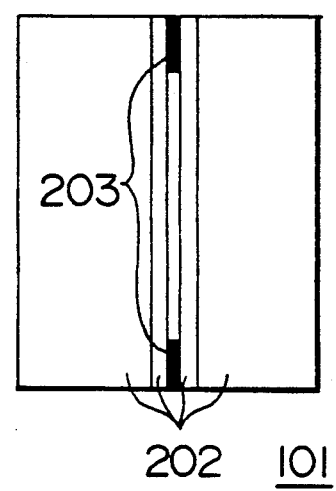
Figure 2C:
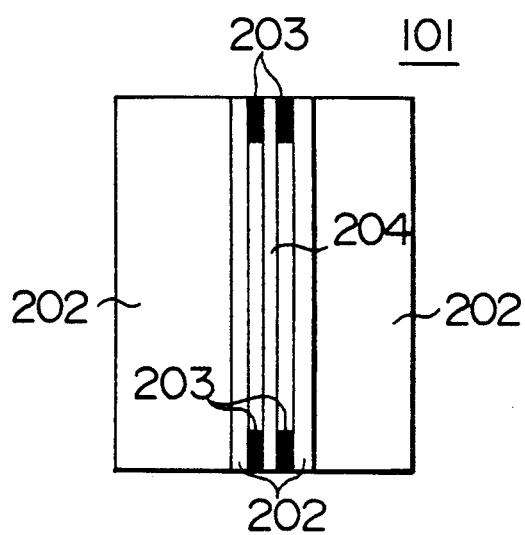

FIGS. 2A, 2B and 2C are a perspective view and a plan view, which show an embodiment of the cell allocation device of the first type in accordance with the present invention; and a plan view showing a modification of the embodiment, respectively. In this embodiment, the first zone of cell allocation device 101 is formed by two glass plates 202 and two spacers 203 and thus distinguished from the second zone. This device 101 is used in close contact with the surface of the culture substrate. By using such device 101, the cells can be allocated repeatedly in a definite width.

In the modification shown in FIG. 2C, glass plate 204 is placed between adjacent spacers 203 as shown. Therefore, two parallel cell lines can be allocated at once in this embodiment.

Materials for the glass plates 202 and 204 and the spacers 203 are not particularly limited but any material may be used so long as it does not inhibit growth of the cells and expression of the functions. As such materials, there may be used, for example, glass, plastic and the like.

Figure 3:
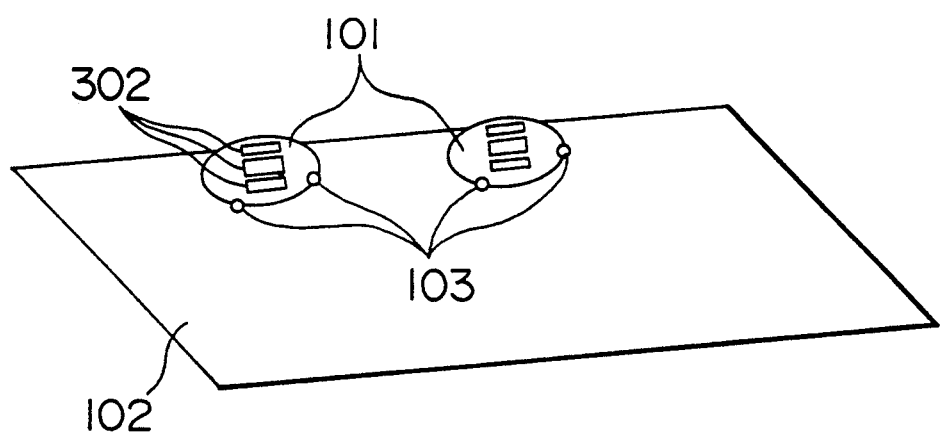
FIG. 3 shows the relationship between another embodiment of the cell allocation device of first type in accordance with the present invention and a culture substrate.

FIG. 3 shows the relationship between another embodiment of the cell allocation device of the first type in accordance with the present invention and the culture substrate.

In this embodiment, each cell allocation device 101 having slits 302 penetrating through both surfaces is placed in close contact with the surface of the culture substrate 102 so that the first zone within the slits on the culture substrate is divided from the second zone masked with the device 101. The device 101 is temporarily fixed on the surface of the culture substrate 102 with dental utility wax 103. Using the cell allocation device 101 having such slits, the cells can be easily allocated even in a complicated pattern.

Figures 4A, 4B:
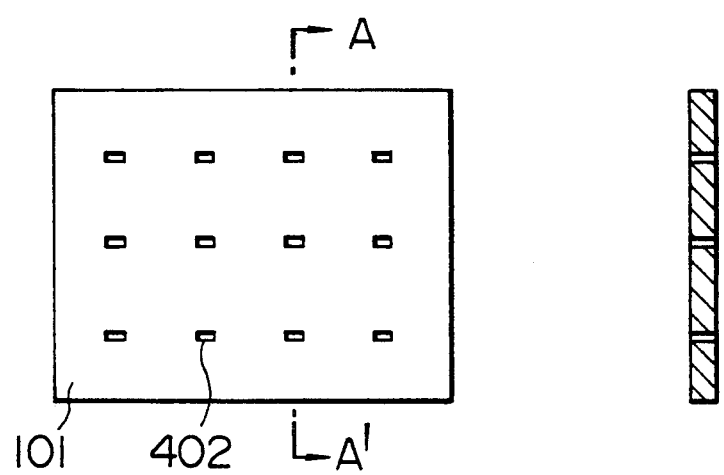
FIGS. 4A and 4B are a plan view and a cross-sectional view, respectively, showing another embodiment of the cell allocation device of first type in accordance with the present invention.

FIGS. 4A and 4B are a plan view and a cross-sectional view, respectively, showing another embodiment of the cell allocation device of the first type in accordance with the present invention.

A number of fine slits 402 are etched on the cell allocation device 101. Using the device 101 having such slits, one or more cells can be easily allocated with a definite interval.

Figure 5A:
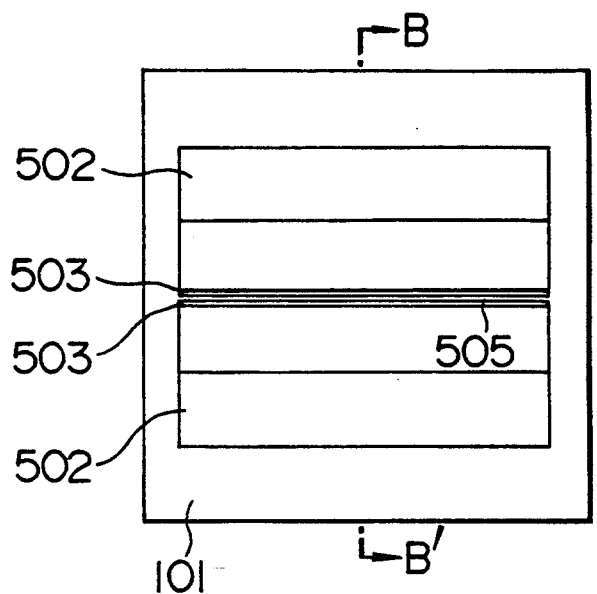
FIGS. 5A and 5B are a plan view and a cross-sectional view, respectively, showing a further embodiment of the cell allocation device of first type in accordance with the present invention.
Figure 5B:
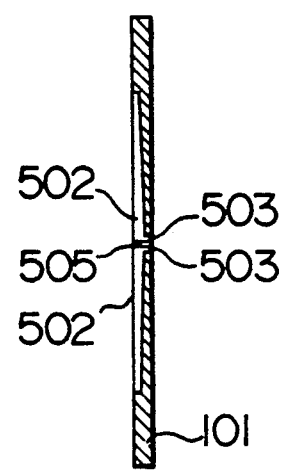

FIGS. 5A and 5B are a plain view and a cross-sectional view, respectively, showing a further embodiment of the cell allocation device of the first type in accordance with the present invention.

The cell allocation device 101 has two chambers 502 which are formed adjacent each other by leaving a narrow partition 505 and are independent from each other. Fine slits 503 independent from each other are etched in device 101 for each of the chambers 502, and pass through both surfaces. After the device 101 is closely contacted with the culture substrate, the chambers 502 are filled up with cell suspensions of different types of cells, respectively. The cells in the suspensions are precipitated on the surface of the culture substrate by centrifugation. Using the cell allocation device 101 having the two slits provided independently from each other, two kinds of cells can be easily allocated on the same surface separately from each other.

Figure 6A:
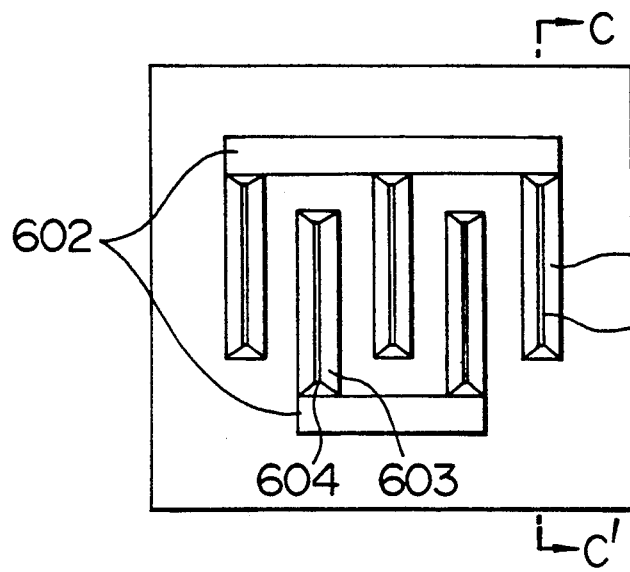
FIGS. 6A and 6B are a plan view and a cross-sectional view, respectively, showing a still further embodiment of the cell allocation device of first type in accordance with the present invention.
Figure 6B:
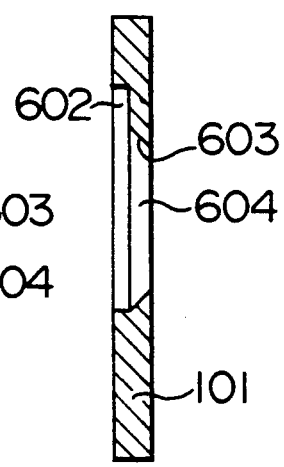

FIGS. 6A and 6B are a plan view and a cross-sectional view, respectively, showing a still further embodiment of the cell allocation device of the first type in accordance with the present invention.

In this embodiment, the cell allocation device 101 has two cell suspension pools 602 which are independent from each other. A plurality of shallow discrete chambers 603 are connected with each of the cell suspension pools 602. A fine slit 604 is etched at the bottom of each of the chambers 603 and passes through both surfaces of device 101. After the device 101 is closely contacted with the culture substrate, the cell suspension pools 602 are filled up with cell suspensions of different kinds of cells, respectively. After the cell suspensions are transferred to each of the chambers 603 connected with each of the pools, the cells in the suspensions are precipitated on the culture substrate by centrifugation. Using the cell allocation device 101 having the two discrete slits, plural kinds of cells can be easily allocated simultaneously on the same surface separately from each other.

Figure 7A:
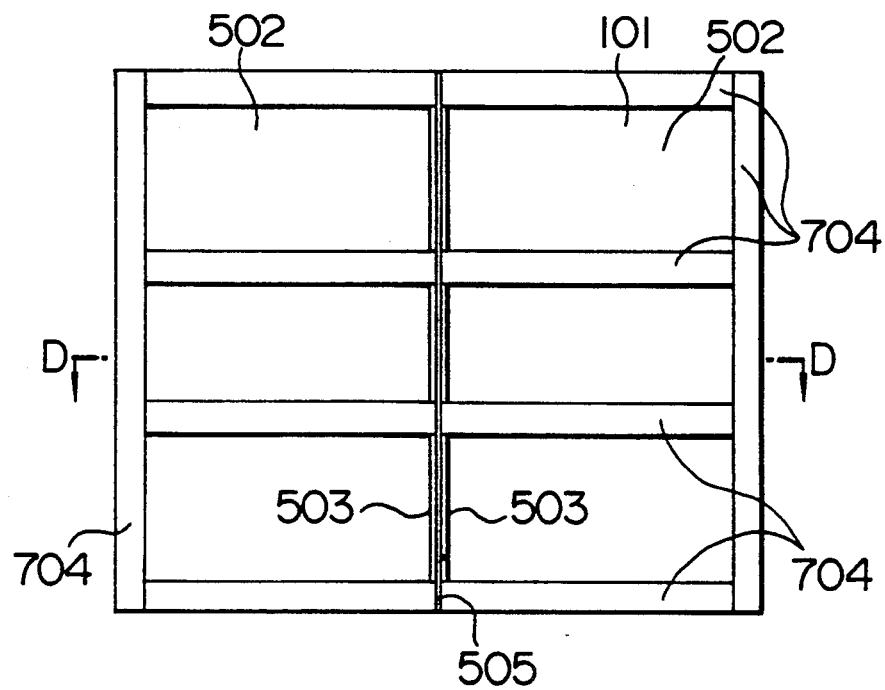
FIGS. 7A, 7B and 7C are a plan view and cross-sectional views, respectively, showing a still further embodiment of the cell allocation device of first type in accordance with the present invention.
Figure 7B:
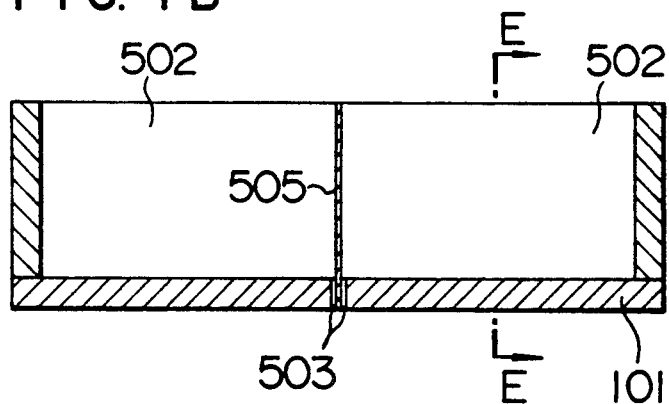
Figure 7C:
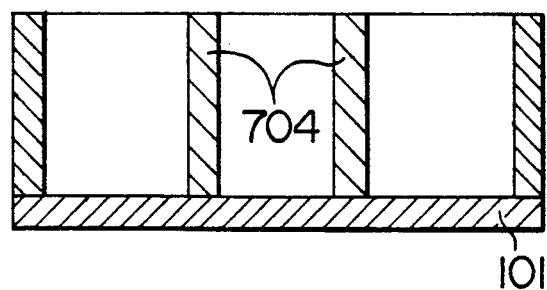

FIGS. 7A, 7B and 7C are a plan view and two cross-sectional views showing a still further embodiment of the cell allocation device of the first type in accordance with the present invention.

This embodiment is a modification of another embodiment of the device of the first type shown in FIGS. 5A and 5B. As shown, a partition between the chambers of the cell allocation device 101 shown in FIG. 5B is made sufficiently high. Members corresponding to those shown in FIGS. 5A and 5B are designated by the same numerals. Numeral 704 indicates supporting plates of the partition 505.

After the device 101 is closely contacted with the culture substrate, the chambers 502 are filled up with cell suspensions of different kinds of cells, respectively. The cells in the suspensions are precipitated on the culture substrate by centrifugation. Using the cell allocation device 101 having the two discrete slits, the cells of plural kinds can be easily allocated in a sufficient length concurrently on the same surface independently from each other.

Next, embodiments of the cell allocation device of the second type according to the present invention are described below. The embodiments of the cell allocation device of the second type are designed to plate on the culture substrate by spontaneous sedimentation with certainty, while in the embodiments of the first type, the cells in the cell suspensions are precipitated and plated onto the surface of the culture substrate by centrifugal force.

FIGS. 8A, 8B, 8C, 8D and 8E are a plan view, a back surface view and a cross-sectional view, respectively, showing an embodiment of the cell allocation device of the second type in accordance with the present invention; and a plan view (or a back view) showing a masking plate for modifying the embodiment and a cross-sectional view when the masking plate is mounted.

Figure 8A:
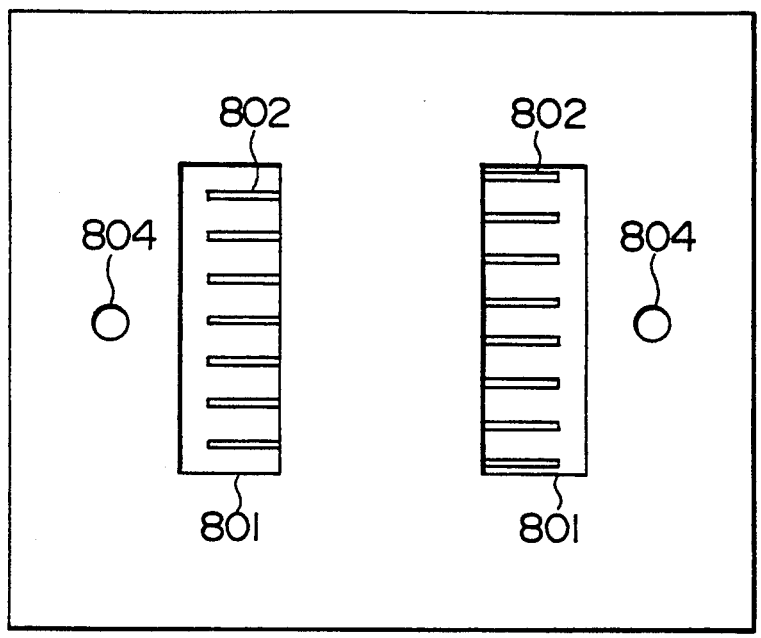
FIGS. 8A, 8B, 8C, 8D and 8E are a plan view, a back surface view and a cross-sectional view, respectively, showing an embodiment of the cell allocation device of second type in accordance with the present invention; and a plan view (or a back view) showing a masking plate for modifying the embodiment and a cross-sectional view when the masking plate is mounted.
Figure 8B:
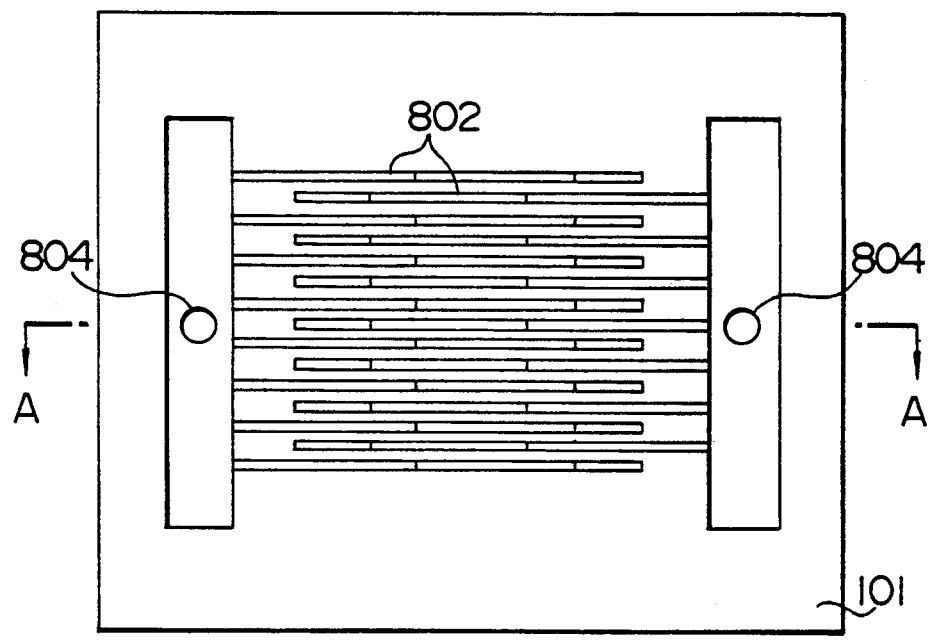
Figure 8C:
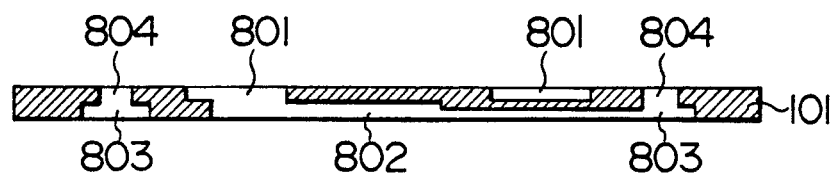

Firstly, the embodiment shown by the plan view, back view and cross-sectional view in FIGS. 8A, 8B and 8C is explained below.

In this embodiment, cell allocation device 101 comprises cell suspension pools 801 etched on the surface, the device zones 802 extended to and connected with the cell suspension pools (the zones 802 are apertures for allocating cells on the culture substrate) etched on the back surface of the device cell suspension recovery pools 803 which are etched on the back surface of the device and connected with the zones 802, and penetrating holes 804 of the cell suspension recovery pools 803 toward the surface of the device.

In the embodiment shown in FIGS. 8A-8C, the zone 802 extended to connect with the cell suspension pool 801 on the left in the figure is allocated alternately with the zone 802 extended to connect with the cell suspension pool 801 on the right in the figure. Therefore, the zone 802 extended to connect with the cell suspension pool 801 on the left connects at the cell suspension recovery pool 803 on the right and also connects with the penetrating hole 804 on the right toward the surface of the plate, in the figure. On the other hand, the zone 802 extended to connect with the cell suspension pool 801 on the right connects at the cell suspension recovery pool 803 on the left and also connects with the penetrating hole 804 on the left toward the surface of the plate, in the figure. After the device 101 is closely contacted with the culture substrate, the cell suspension is fed to the cell suspension pool 801 through the upper surface of the device 101, enters into the zone 802 located beneath the device 101, then enters the cell suspension recovery pool 803 located beneath the device 101 and finally reaches the upper surface of the device 101 through the penetrating hole 804.

That is, in this embodiment, the pathway through which the cell suspension passes is not closed when viewed from the upper surface of the cell allocation device 101. It is thus possible to perform the operation of sucking the cell suspension from the upper surface of the device 101 of the penetrating hole 804, while dropping the cell suspension onto the cell suspension pool 801 from above the device 101. By repeating the operation several times, a cell density of the cell suspension in the zone 802 can be made uniform. After the cells in the zone 802 are precipitated and adhered on the surface of the substrate, the operation described above is then gently performed, whereby the cells in the zone 802 can be precipitated and plated onto the surface of the substrate.

The cell allocation device 101 thus constructed may also be used in combination with the method of rapid allocating by centrifugal force, when the cell density of the cell suspension cannot be increased.

In this embodiment, as described above, the zones 802 connected with the cell suspension pools 801 located on the left and right of the cell sorting element plate are independent from each other. Therefore, when suspensions of different kinds of cells are fed to each of the cell suspension pools 801 located on the left and right, a plural number of sets of different types of cells can be allocated alternately in an adjacent belt-like shape. In addition, since the cell allocation device can be used repeatedly, it is possible to provide the cell allocating of quite the same shape on different substrates in combination of different cells.

In this embodiment, a zone 802 having a width of 200 $\mu$m and a depth of 400 $\mu$m is etched on a silicon wafer having a thickness of 800 $\mu$m, by applying technology for preparing semiconductors. Even the cell allocation device having such a complicated shape can be easily prepared by preparing several resist patterns and performing an etching step several times, while accurately registering the resist patterns on the silicon wafer. Of course, materials for this type of cell allocation device are not particularly limited but any material may be used so long as it does not inhibit growth of the cells and expression of the functions. These materials may be not only silicon but also, for example, plastic, glass and the like.

Figure 8D:
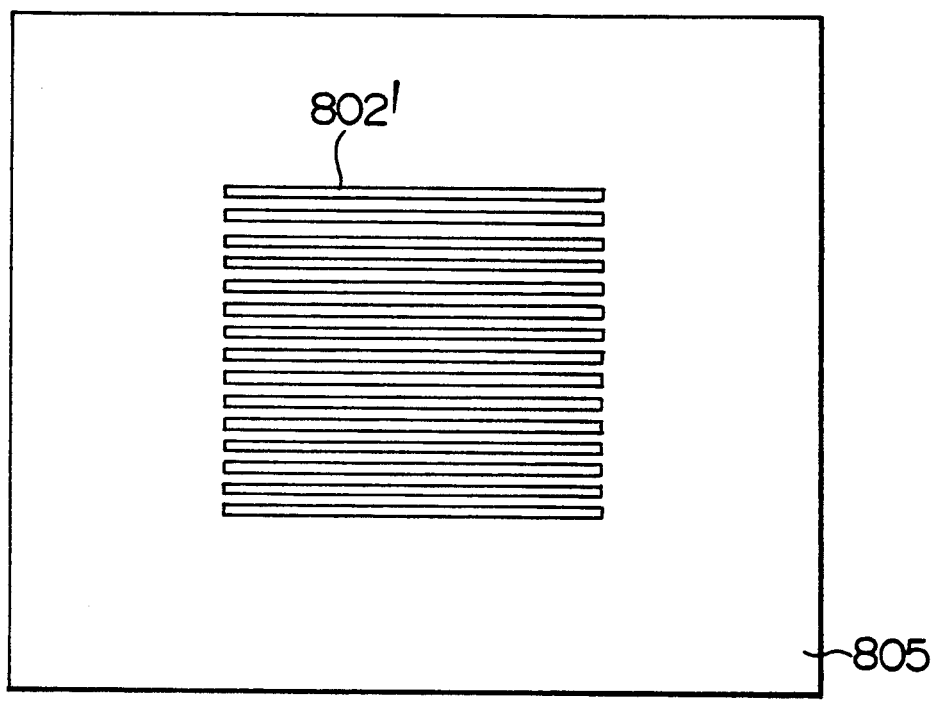
Figure 8E:
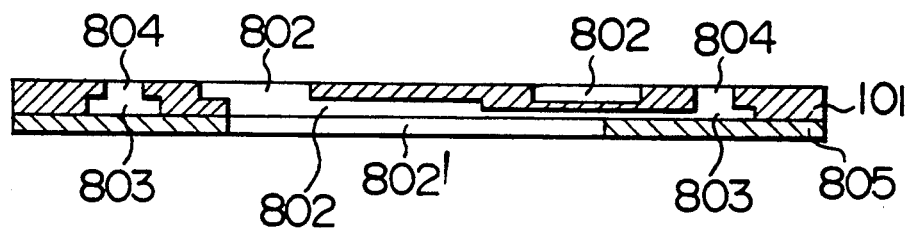

Next, the modification shown in FIGS. 8D and 8E is explained below.

In the embodiment described above, the cell suspension recovery pool 803 is open to the culture substrate so that the cell lanes allocated in parallel on the culture substrate are connected at the positions corresponding to the apertures. In order to make all of the cell lanes allocated in parallel on the culture substrate to be independent from each other, the structure may be designed so that the apertures are masked for the culture substrate.

FIG. 8D is a plan view showing an example of the masking plate. The masking plate 805 has cutout 802' corresponding to the zone 802 on the cell allocation device 101. The masking plate 805 is adhered to the bottom surface of the cell allocation device 101 and used, as shown in FIG. 8E. Then, the cell allocating as shown in FIG. 8D is obtained. That is, the cell lanes allocated in parallel on the culture substrate can be made all independent from each other.

In using this type of cell allocation device 101, it is appropriate that the culture substrate is encased in a culture dish made of, e.g., plastic, etc., having a definite depth, the device 101 is mounted in close contact with the culture substrate, the cell suspension is then introduced into the cell allocation device as described above to precipitate the cells, and the cell allocation device is withdrawn from the substrate.

Figure 9:
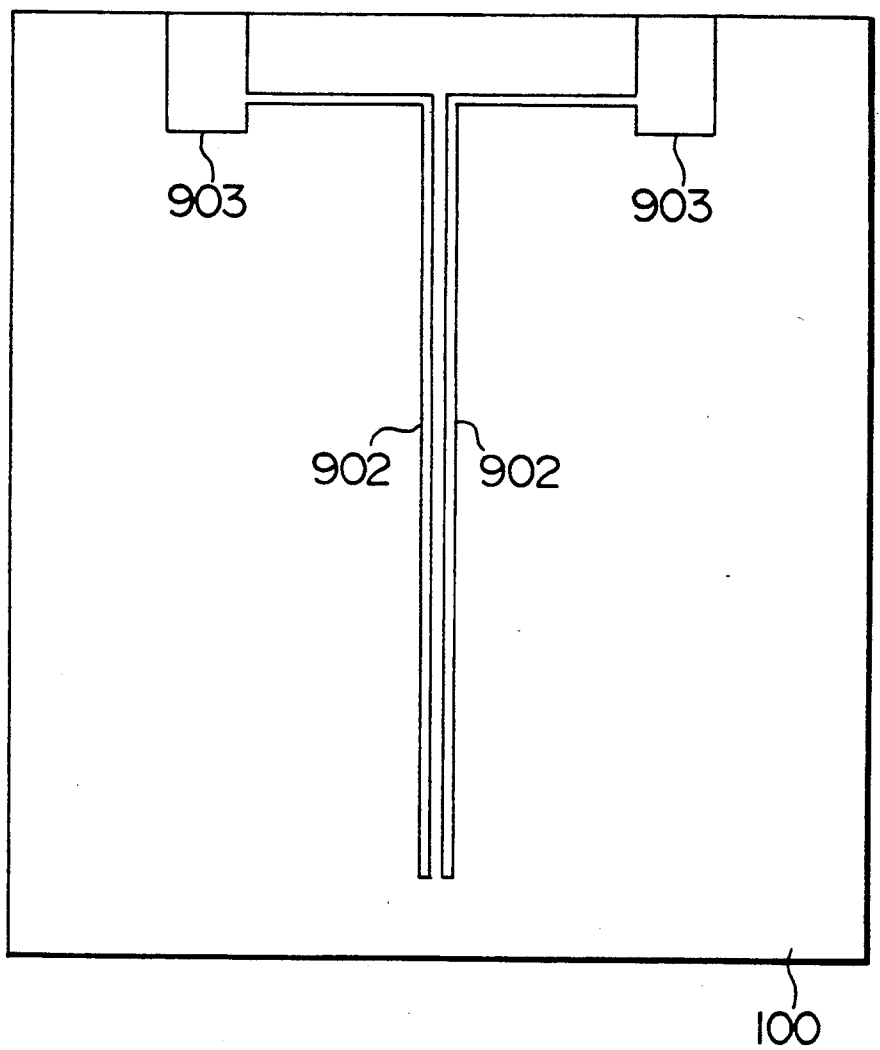
FIG. 9 is a plan view showing an embodiment of the culture substrate in accordance with the present invention.

FIG. 9 is a plan view showing an embodiment of the culture substrate in accordance with the present invention.

In this embodiment, electrodes are provided to output the function of the cells, allocated and cultured on the surface of the culture substrate. The culture substrate of this embodiment comprises glass plate 100, patterned platinum electrodes 902 present on glass plate 100, and platinum-made ports 903 for electrically connecting the platinum electrodes 902 with an outside wire.

On the culture substrate, the number of patterned platinum electrodes 902 and platinum-made ports 903 can be freely set forth but when the number coincides with that of the zones on the cell allocation device 101, cells of different kinds, especially neurons, can be allocated on the platinum electrodes 902 which are independent from each other. Therefore, the response of each cell to an electrical signal can be independently observed. This observation can be made using the platinum electrodes 902 in contact with the cells so that the cells are hardly damaged. It is thus possible to make the observation over long periods of time.

Cell sorting in each embodiment and the results of culture tests are described below.

Experiment 1

Using the device shown in FIG. 1, cells were allocated.

In a plastic dish having a diameter of 35 mm and a depth of 10 mm, culture substrate 102 of 22 mm×24 mm was laid. Two stainless steel shaving blades having a length of 16 mm and a width of 10 mm were used as cell allocation device 101, and mounted to provide a gap of about 500 $\mu$m, as shown in FIG. 1. After sterilization with alcohol, 2 ml of PIT medium (Manual of Serum Free Cell Culture, page 197; published by Kodansha Scientific) was added to the dish and 0.5 ml of rat cerebellar cell suspension in a cell density of about $1 \times 10^6$ cells/ml was further dropped into the space between the shaving blades 101. After centrifugation at 1000 rpm for three minutes, the system was allowed to stand in an incubator to adhere the cerebellar cells on the surface of the culture substrate 102. Two hours later, the shaving blades 101 were withdrawn and the state of cells allocated on the surface of the culture substrate was observed. Then, the system was cultured in an incubator for 22 hours and the state of the cells on the surface of the culture substrate 102 was again observed.

The results are shown by pictures in FIGS. 10 and 11. FIG. 10 is a picture showing the state of the cells allocated on the surface of the culture substrate two hours after initiation of the culture; and FIG. 11 is a picture showing the state of the cells allocated on the surface of the culture substrate 24 hours after initiation of the culture. From FIG. 10 it is noted that the cerebellar cells could be allocated in a width of 500 μm, when using the device of the present invention. In FIG. 11, neurons in the cerebellum extend neurites to about 100 μm and it is further noted that, using the device of the present invention, the cells could be allocated without causing any damage.

Experiment 2

Cells were allocated using the device shown in FIG. 2.

Cell allocation device 101 having a glass slit as shown in FIG. 2 was prepared using 4 glass plates 202 having a length of 24 mm, a width of 7 mm and a thickness of 1.2 mm, and a glass-made spacer 203 having a thickness of 200 μm. In a plastic dish having a diameter of 35 mm and a depth of 10 mm, a culture substrate 102 of 22 mm×24 mm was laid. The cell allocation device 101 was fixed on the culture substrate in close contact therewith. After sterilization with alcohol, 2 ml of PIT medium was added to the dish and 0.5 ml of rat cerebellar cell suspension in a cell density of about $1\times10^6$ cells/ml was further dropped onto the slit. After centrifugation at 1000 rpm for three minutes, the system was allowed to stand in an incubator to adhere the cerebellar cells on the surface of the culture substrate. One hour later, the device 101 was withdrawn. After culturing for another 55 hours, the state of the cells on the surface of the culture substrate was observed.

The results are shown by a picture in FIG. 12. From FIG. 12 it is noted that the cerebellar cells could be sharply allocated in a width of 200 μm, when using the device of the present invention. It is also noted that using the device of the present invention, the cells could be allocated without causing any damage, since neurons in the cerebellum extend neurites to about 150 μm. Furthermore, the device could be used repeatedly.

Experiment 3

Cells were allocated using the device shown in FIG. 3.

In a plastic dish having a diameter of 35 mm and a depth of 10 mm, a culture substrate 102 of 22 mm×24 mm was laid. Copper-made electron microscope grids having a diameter of 3 mm and a thickness of 0.03 mm were mounted at the cell allocation device 101, as shown in FIG. 3. Each grid has 3 slits 302 of 2200 μm long and 100 μm, 350 μm and 100 μm wide, respectively. After sterilization with alcohol, 2 ml of PIT medium supplemented with 10% serum was added to the dish and 0.5 ml of IMR-32 cells (nueroblastoma-derived cells) in a cell density of about $1\times10^6$ cells/ml were dropped around the grids. After centrifugation at 1000 rpm for three minutes, the system was allowed to stand in an incubator to adhere the cerebellar cells on the surface of the culture substrate 102. Two hours later, the grids 301 were withdrawn, and the state of the cells on the surface of the culture substrate 102 was observed.

The results are shown by a picture in FIG. 13. It is noted that the cells could be allocated in the width of the slit.

Experiment 4

Using the device equipped with the substrate shown in FIG. 4, cells were allocated.

In a plastic dish having a diameter of 35 mm and a depth of 10 mm, a culture substrate of 22 mm×24 mm was laid. A silicon-made plate having a length of 14 mm, a width of 24 mm and a thickness of 0.4 mm was mounted to the substrate as cell allocation device 101. Slits, each having a length of 30 μm and a width of 100 μm, were etched with an interval of 600 μm long and 800 μm wide on the device 101. After sterilization with alcohol, 2 ml of PIT medium supplemented with 200 ng/ml NGF (nerve growth factor) was added to the dish and 0.5 ml of mouse dorsal root ganglion suspension in a cell density of about $1\times10^6$ cells/ml was dropped onto the element plate 101. After centrifugation at 1000 rpm for three minutes, the system was allowed to stand in an incubator to adhere the cells on the surface of the culture substrate. Two hours later, the element plate 101 was withdrawn and the start of cell allocating was observed on the culture substrate. After culturing for another 16 hours, the state of the cells was again observed on the culture substrate.

The results are shown by pictures in FIGS. 14 and 15. FIGS. 14 and 15 show the state of the cells allocated on the surface of the culture substrate two hours after and 18 hours after initiation of the culture, respectively. From FIG. 14 it is noted that the dorsal root ganglion cells could be allocated one by one or more substantially in the slit portions. It is also noted from FIG. 15 that, using the device of the present invention, the cells could be allocated without causing any damage, since neurons of the dorsal root ganglion extend neurites to about 400 μm.

Experiment 5

Using the cell allocating element 101 shown in FIG. 8, cells were allocated using spontaneous sedimentation due to gravity.

After sterilization with alcohol, the cell allocation device 101 was fixed on a culture substrate of 22 mm×24 mm, which had been laid on a plastic culture dish having a diameter of 35 mm and a depth of 10 mm, in close contact with the substrate. Then, 2 ml of PIT medium was added to the culture dish and 0.2 ml of rat embryo hippocampal neuron suspension in a cell density of about $1\times10^7$ cells/ml were introduced into cell suspension pools 801. The system was allowed to stand for 30 minutes in a $CO_2$ incubator to precipitate and adhere the hippocampal cells on a glass surface serving as culture substrate. Then, the device 101 was withdrawn from the glass surface. After culturing for another 70 hours, the state of the cells was observed on the glass surface.

Figure 16A:
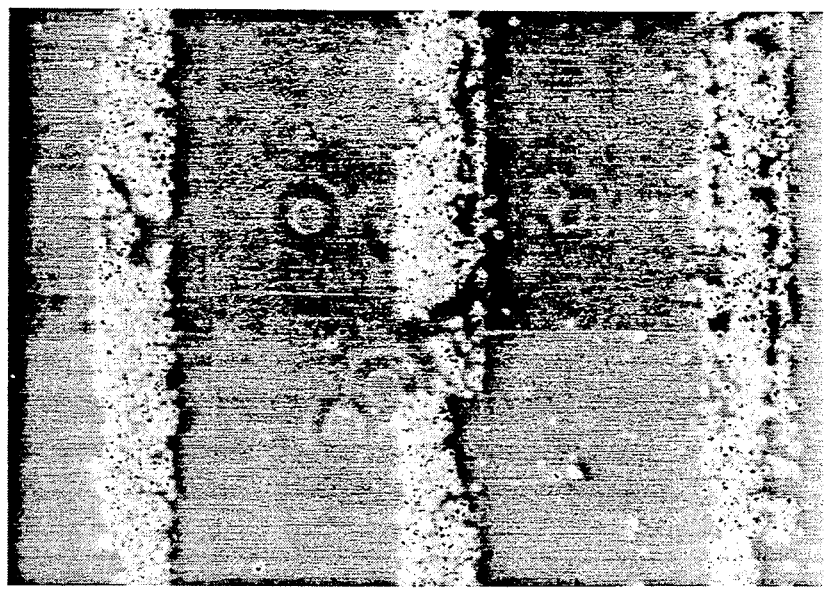
FIG. 16A and 16B are pictures showing the state of the cells allocated on the surface of the culture substrate according to the embodiment shown in FIG. 8, immediately after the cell allocating and 70 hours after initiation of the culture, respectively.
Figure 16B:
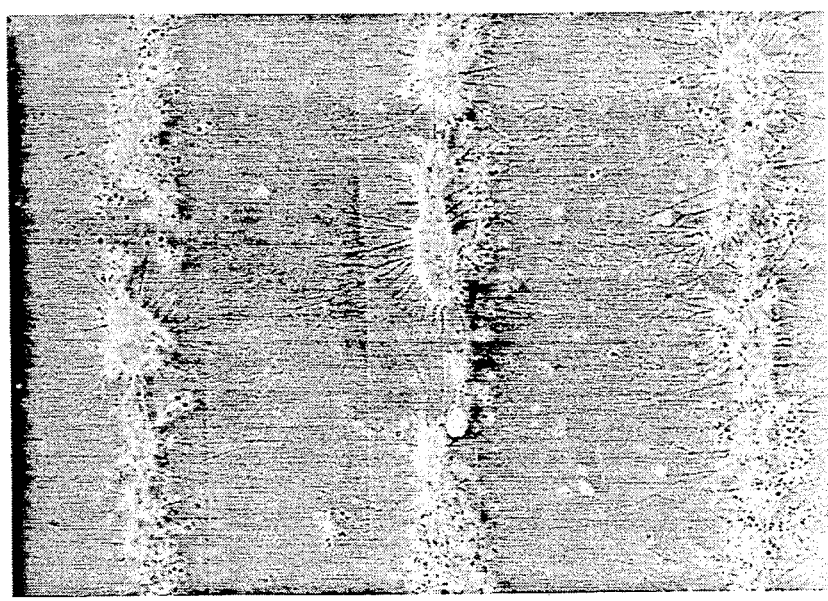

The results are shown by pictures in FIGS. 16A and 16B. FIGS. 16A and 16B show the state of the cells allocated on the glass surface culture substrate immediately after the cell allocation device 101 was withdrawn from the glass surface and the state of the cells 70 hours after initiation of the culture, respectively.

From FIG. 16A it is noted that when using the device, the hippocampal cells could be allocated only for 30 minutes by spontaneous sedimentation. This is because the height of the zone 802 in the device 101 is as low as 400 μm from the surface of the substrate and a distance for the sedimentation is short. It is also noted from FIG. 16B that the method for allocating by spontaneous sedimentation using the device does not injure the cells, since hippocampal neurons extend many long fibers.

Experiment 6

Using the cell allocating element 101 shown in FIG. 8, cells were allocated by precipitation due to centrifugal force.

After sterilization with alcohol, the cell allocation device 101 was fixed on a culture substrate of 22 mm×24 mm, which had been laid on a plastic culture disk having a diameter of 35 mm and a depth of 10 mm, in close contact with the substrate. Then, 2 ml of PIT medium was added to the culture dish and 0.2 ml each of chick embryonic retina and optic tectum cell suspensions in a cell density of about $1 \times 10^7$ cells/ml were separately introduced into cell suspension pools 801 different from each other. After centrifugation at 1000 rpm for three minutes, the system was allowed to stand in a $CO_2$ incubator to adhere the cells on the glass surface as culture substrate. Two hours later, the device 101 was withdrawn from a glass surface serving as the culture substrate. After culturing for another 88 hours in a $CO_2$ incubator, the state of the cells was observed on the glass surface.

Figure 17A:
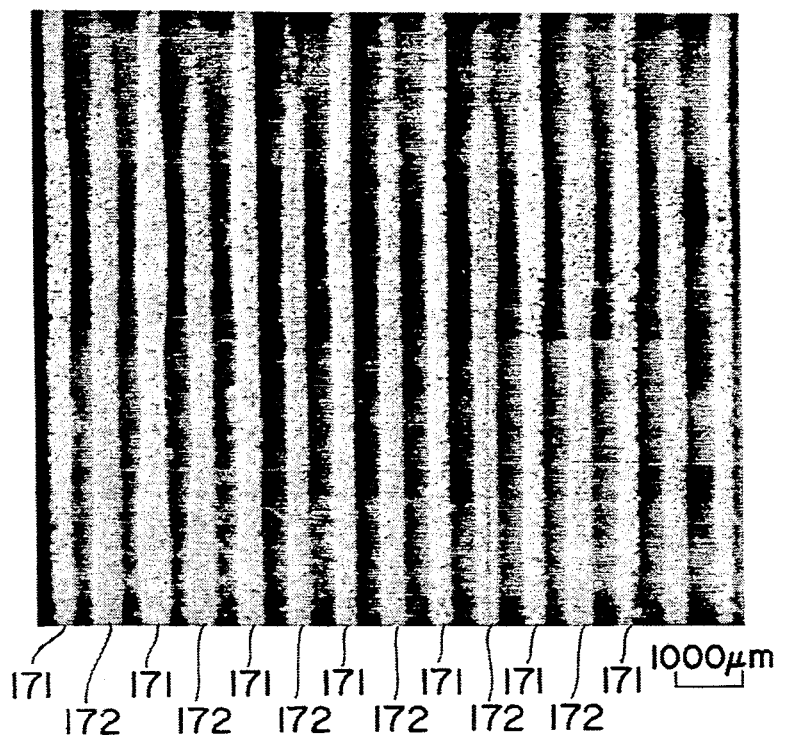
FIGS. 17A and 17B are pictures showing the state of the cells allocated on the surface of the culture substrate according to the embodiment shown in FIG. 8, immediately after the cell allocating and 90 hours after initiation of the culture, respectively.
Figure 17B:
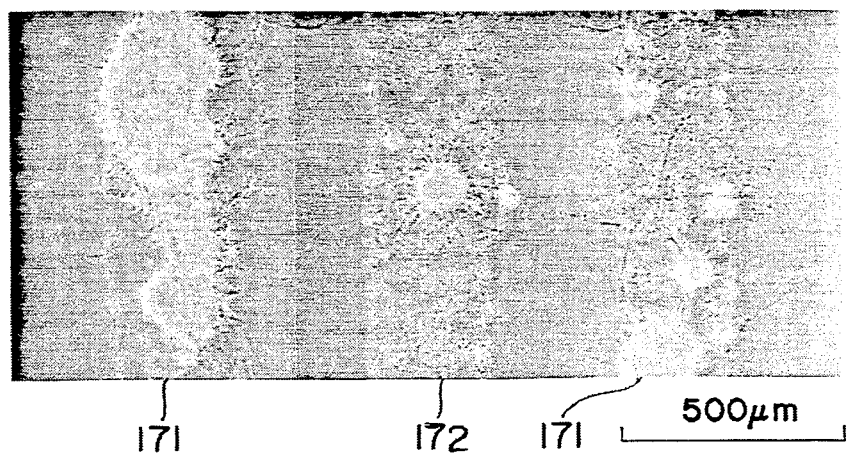

The results are shown by pictures in FIGS. 17A and 17B. FIGS. 17A and 17B show the state of the cells allocated on the glass surface culture substrate immediately after the device 101 was withdrawn from the glass surface and the state of the cells 90 hours after initiation of the culture, respectively. In the figure, numeral 171 denotes retinal cells and numeral 172 denotes tectal cells. From FIG. 17A it is noted that when using the device, nerve cells of different kinds could be allocated alternately in a belt shape by precipitation due to centrifugal force. This is because the planar property of the back surface of this element 101 is extremely good and closely contacted to the surface of the substrate. Furthermore, distribution of the retinal cells, which had been previously labeled with fluorescent rhodamine 6G, was fluorometrically observed immediately after the device 101 was withdrawn from the glass surface. The retinal cells had not significantly strayed into the tectal cell zone. It is also noted from FIG. 17B that the method for allocating by precipitation due to centrifugal force using the device does not injure the cells, since the retinal and tectal neurons extend nerve fibers.

Experiment 7

Using the culture substrate shown in FIG. 9 and the cell allocation device shown in FIG. 8, cells were allocated by precipitation due to centrifugal force.

After sterilization with alcohol, the cell allocation device 101 was fixed on the culture substrate of 22 mm×24 mm shown in FIG. 9, which had been laid on a plastic culture dish having a diameter of 35 mm and a depth of 10 mm, in close contact with the substrate. Then, 2 ml of PIT medium were added to the culture dish and 0.2 ml each of chick embryonic retina and optic tectum cell suspensions in a cell density of about $1 \times 10^7$ cells/ml were separately introduced into cell suspension pools 801 different from each other. After centrifugation at 1000 rpm for three minutes, the system was allowed to stand in a $CO_2$ incubator to adhere the cells on a glass surface serving as the culture substrate. Two hours later, the device 101 was withdrawn from the glass surface. After culturing for another 68 hours in a $CO_2$ incubator, the state of the cells was observed on the glass surface.

The results are shown by a picture in FIG. 18. FIG. 18 shows the state of the cells allocated on the glass surface culture substrate 70 hours after initiation of the culture. In the figure, numeral 171 denotes retinal cells, numeral 172 denotes tectal cells and numeral 182 denotes platinum electrodes. From FIG. 18 it is noted that when using the culture substrate and cell allocation device 101 of the present invention, cells of different kinds could be allocated on each of the platinum electrodes 902. It is also noted that long-term culture can be performed and synaptic connections between neurons of different kinds can be formed. Furthermore, distribution of the retinal cells, which had been previously labeled with fluorescent rhodamine 6G, was fluorometrically observed immediately after the device 101 was withdrawn from the glass surface culture substrate. The retinal cells had not significantly strayed into the tectal cell zone. It is also confirmed that when electrical stimulation was applied to the retinal cell group through the platinum electrode 182, response of the tectal cell group could be recorded from the other platinum electrode 182.

The foregoing results show that, when using the culture substrate and cell allocation device 101 of the present invention, cells of different kinds can be allocated and cultured independently on each of the platinum electrodes. The results also reveal that it is possible to apply electrical stimulation and, at the same time, record the response of the neurons, via the platinum electrodes 182.

According to the method of the present invention, cells of one or more kinds can be allocated on the same surface of the culture substrate at a specified zone(s), without damaging the cells. Therefore, the method of the present invention provides a practical means for artificially allocating the cells once dissociated and reconstructing the in vivo order. Accordingly, by culturing the cells allocated by the method of the present invention, the functions possessed by the cells can be expressed. For example, a simple neural circuit can be constructed so that the neurons are alive. This circuit can be per se used as a bio-chip or a neurocomputer and can also be used as an input and output interface of a bio chip device prepared by arraying proteins.

We claim:

1. A method for allocating cells on a cell culture substrate comprising the steps of:
   providing a cell culture substrate;
   providing a cell allocation device, including a plate material having a first slit of a construction such that a cell suspension precipitates into the first slit by capillary action and to a first zone on the cell culture substrate;
   providing a cell suspension, containing the cells to be cultured, to the cell allocation device;
   allowing the cells suspended in the cell suspension to allocatingly precipitate to the first zone via the first slit; and
   withdrawing said device;
   wherein a slit is defined as an aperture having first and second linear coplanar dimensions, the first dimension being substantially longer than the second dimension.

2. A method for cell allocation according to claim 1, wherein said device is temporarily fixed on said cell culture substrate.

3. A method of allocating cells according to claim 2, wherein said culture substrate is of a material which is selected from glass, plastic and silicon, and said substrate material is coated with cell-adhesive polypeptides or proteins on the surface thereof; a conductive material is present discretely at predetermined zones on the surface of said culture substrate that overlap at least a part of the first zone and is in contact at the predetermined zones independent from each other; and said culture substrate contains electrodes electrically connected with said conductive material.

4. A method for cell allocation according to claim 1, wherein said plate material comprises a plurality of elements placed nearby each other to define said first slit.

5. A method of allocating cells according to claim 4, wherein said culture substrate is of a material which is selected from glass, plastic and silicon, and said substrate material is coated with cell-adhesive polypeptides or proteins on the surface thereof; a conductive material is present discretely at predetermined zones on the surface of said culture substrate that overlap at least a part of the first zone and is in contact at the predetermined zones independent from each other; and said culture substrate contains electrodes electrically connected with said conductive material.

6. A method of allocating cells according to claim 1, wherein said culture substrate includes one of glass, plastic and silicon coated with a cell-adhesive polypeptide or protein on the surface thereof.

7. A method of allocating cells according to claim 1, wherein said culture substrate includes one of glass, plastic and silicon coated with a cell-adhesive polypeptide or protein on the surface thereof; and further comprising the step of providing a conductive material at discrete locations on the surface of said culture substrate so as to overlap at least a part of the first zone; wherein said culture substrate contains input and output electrodes respectively electrically connected with said conductive material at respective ones of said discrete locations.

8. A method for allocating cells as claimed in claim 7, wherein the cell allocation device-providing step is performed so that the plate material includes a second slit through which cells are to be provided to a second zone on the cell culture substrate, said second slit having a construction such that cells in a cell suspension precipitate into the second slit by capillary action;
wherein the conductive material is further provided to contact the first and second zones independently of each other.

9. A method for allocating cells as claimed in claim 1, wherein the cell allocation device-providing step is performed so that the first slit is less than or equal to about 500 µm wide.

10. A method for allocating cells as claimed in claim 1, wherein the cell allocation device-providing step is performed so that the cell allocation device includes first and second substantially planar plates formed of said plate material and spaced to form the first slit between adjacent ends of the first and second plates, said first and second plates further being arranged so that corresponding portions remote from the first slit define a top side gap that is wider than the first slit.

11. A method for allocating cells as claimed in claim 10, wherein the first and second plates are further arranged at an angle with respect to each other so that the distance between them decreases from the top side gap to the first slit.

12. A method for allocating cells as claimed in claim 1, wherein the cell allocation device-providing step is performed so that the cell allocation device further includes a concavity in communication with the first slit, for enabling a cell suspension pool to be formed in the concavity.

13. A method for allocating cells as claimed in claim 12, wherein the cell allocation device-providing step is performed so that the cell allocation device further includes a second slit in communication with the concavity, said second slit having a construction such that cells in the cell suspension pool precipitate into the second slit by capillary action and to a second zone on the cell culture substrate.

14. A method of allocating cells according to claim 1, wherein said culture substrate is of a material which is selected from glass, plastic and silicon, said substrate material is coated with cell-adhesive polypeptides or proteins on the surface thereof; a conductive material is present discretely at predetermined zones on the surface of said culture substrate that overlap at least a part of the first zone and is in contact at the predetermined zones independent from each other; and said culture substrate contains electrodes electrically connected with said conductive material.

15. A cell allocation device for allocating cells on a cell culture substrate, comprising:
a plate material of a definite shape having a definite width and length, having slits connected through a first surface of the plate material and having a definite thickness, wherein a slit is defined as having first and second linear coplanar dimensions, the first dimension being substantially longer than the second dimension such that cells contained in a cell suspension pass into the slits by capillary action;
a plurality of apertures for respectively connecting a first end of each said slit with a second surface of said plate material; and
a plurality of cutouts for respectively connecting a second end of each said slit with the first surface of said plate material and connecting the second end of each said slit with the second surface of said plate material at sites different from said plurality of apertures.

16. A cell allocation device according to claim 15, further comprising:
a masking plate operably associated with said first surface having slits at substantially the same respective positions as the slits of said plate material.

17. A method for allocating cells on a cell culture substrate using a cell allocation device according to claim 15, comprising the following steps of:
providing a cell culture substrate;
placing said cell allocation device on said cell culture substrate;
introducing a cell suspension into some of said plurality of apertures; and,
withdrawing said cell allocation device.

18. A method of allocating cells according to claim 17, wherein said culture substrate is of a material which is selected from the group consisting of glass, plastic and silicon, and said substrate material is coated with cell-adhesive polypeptides or proteins on a surface thereof; and further comprising the steps of providing a conductive material discretely at predetermined zones on a surface of said culture substrate to overlap at least some of the plurality of cutouts of the cell allocation device, and in contact at the predetermined zones independent from each other; and providing said culture substrate with at least one electrode electrically connected with said conductive material.

19. A method for allocating cells on a cell culture substrate according to claim 17, further comprising the step of, after introducing the cell suspension into said some of said plurality of apertures, applying a centrifugal force to said cell allocation device and said cell culture substrate.

20. A method for allocating cells as claimed in claim 19, wherein said step of applying a centrifugal force is performed for three minutes or less, at a speed of less than or equal to 1200 RPM.

21. A method for allocating cells according to claim 19, wherein said culture substrate is of a material which is selected from the group consisting of glass, plastic and silicon, and said substrate material is coated with cell-adhesive polypeptides or proteins on a surface thereof; and further comprising the steps of providing a conductive material discretely at predetermined zones on a surface of said culture substrate to overlap at least some of the plurality of cutouts of the cell allocation device, and in contact at the predetermined zones independent from each other; and providing said culture substrate with at least one electrode electrically connected with said conductive material.

22. A cell allocation device for allocating cells on a culture substrate, comprising:
first and second planar articles, each having front and back surfaces and a four-sided perimeter; and
means for removably attaching the first and second planar articles to a culture substrate at respective angles to the culture substrate so that one side of each planar article perimeter is adjacent to the culture substrate and to each other to form a gap between the adjacent perimeter sides suitable for cells in a cell suspension to pass into the gap by capillary action for allocation on the culture substrate.

23. A cell allocation device for allocating cells on a culture substrate, comprising:
first and second substantially L-shaped members, each L-shaped member including a pair of planar articles joined at respectively associated edges to form an L shape wherein each L-shaped member is arranged so that a planar article of each L-shaped member faces a corresponding planar article of the other L-shaped member; and
spacer means for maintaining a gap suitable for admitting cells in a cell suspension by capillary action for allocation on the culture substrate between the facing planar articles of the first and second L-shaped members.

24. A cell allocation device as claimed in claim 23, wherein said spacer means includes first and second spacers arranged between, and in contact with both of, the facing planar articles of the first and second L-shaped members.

25. A cell allocation device as claimed in claim 23, wherein said spacer means includes a planar member arranged between, and facing both of, the first and second L-shaped members; first and second spacers arranged between, and in contact with both of, the facing planar article of the first L-shaped member and the planar member; and third and fourth spacers arranged between, and in contact with both of, the planar member and the facing planar article of the second L-shaped member.

26. A cell allocation device for allocating cells on a culture substrate, comprising:
an article having substantially planar first and second surfaces and at least one cell allocation zone including first zone walls and second zone walls, recessed from said first surface, wherein the walls of each zone slope downwardly from said first surface to respective apertures formed in the second surface;
wherein said first and second sloped recessed zone walls and said apertures are arranged to conduct cells in a cell suspension down into the apertures by capillary action, to be allocated on the culture substrate.

27. A cell allocation device as claimed in claim 26, wherein the substantially first surface further includes a plurality of troughs, distinct from said apertures and said zone walls, communicating with at least one said cell allocation zone.

28. A cell allocation device for allocating cells on a culture substrate, comprising:
a floor, a perimeter wall contacting and extending at an angle to said floor, and a plurality of inner walls contacting and extending at an angle to said floor so as to define, with said floor, a plurality of chambers;
wherein each of said chambers includes a cell allocation zone which is defined in part by a partition; and includes an aperture formed in the floor into which cells in a cell suspension pass by capillary action for allocation on the culture substrate, and through which said partition extends to contact the culture substrate.

29. A cell allocation device as claimed in claim 28, wherein the partition contributes to defining two adjacent chambers by isolating the respective apertures of the two adjacent chambers from each other so that cells are allocated on the culture substrate via the adjacent apertures without commingling.

30. A cell allocation device for allocating cells on a cell culture substrate, comprising:
a plate material having a first slit through which cells are to be provided to a first zone on the cell culture substrate;
wherein a slit is defined as an aperture having first and second linear coplanar dimensions, the first dimension being substantially longer than the second dimension such that the slit is suitable for cells in a cell suspension to pass thereinto by capillary action.

31. A cell allocation device as claimed in claim 30, wherein the first slit is less than or equal to about 500 μm wide.

32. A cell allocation device as claimed in claim 30, wherein the plate material includes first and second substantially planar plates formed of said plate material and arranged to form the first slit between adjacent edges of the first and second plates, said first and second plates being further arranged to form a top side gap at respective corresponding portions remote from the first slit, wherein said top side gap is wider than the first slit.

33. A cell allocation device as claimed in claim 32, wherein the first and second plates are arranged at an angle with respect to each other so that the distance between the plates decreases from the top side gap to the first slit.

34. A cell allocation device as claimed in claim 30, further comprising a concavity formed in the plate material in communication with the first slit, for enabling a cell suspension pool to be formed in the concavity.

35. A cell allocation device as claimed in claim 34, wherein the plate material includes a second slit through which cells are to be provided to a second zone on the cell culture substrate, wherein the concavity is further in communication with the second slit.

36. A method for allocating cells on a cell culture substrate, comprising the steps of:
providing a cell culture substrate;
providing a cell allocation device including a plate material having a cutout connected throughout from a first surface of the plate material to a second surface of the plate material, and a concavity provided in communication with said cutout for maintaining a cell suspension pool in the concavity, said cutout being formed by a photolithographic etch;
providing a cell suspension containing cells to be cultured to said concavity;
allowing the cells to precipitate to the cell culture substrate via the cutout; and
withdrawing said device.

37. A cell allocation device, comprising:
a plate material having a cutout connected throughout from a first surface of the plate material to a second surface of the plate material such that cells in a cell suspension pass into the cutout by capillary action, and a concavity provided in communication with said cutout for maintaining a cell suspension pool in the concavity.

38. A cell allocation device as claimed in claim 37, wherein said plate material includes a silicon wafer, and said cutout is formed in the silicon wafer by photolithography.

39. A method for allocating cells on a cell culture substrate, comprising the steps of:
providing a cell culture substrate;
providing a cell allocation device including a plate material having first and second surfaces, a first concavity in the first surface of the plate material for maintaining a first cell suspension pool in the first concavity, a second concavity in the second surface of the plate material, and a first plurality of longitudinal cutouts in the second surface connected to the first concavity by a penetrating hole; said first plurality of longitudinal cutouts being constructed such that cells in a cell suspension pass thereinto by capillary action, and being connected in parallel between the first concavity and the second concavity;
providing a first cell suspension containing cells to be cultured to said first concavity;
allowing the cells of the first cell suspension to precipitate to the cell culture substrate via the first plurality of longitudinal cutouts and to pool on the cell culture substrate at the second concavity; and
withdrawing said device.

40. A method for allocating cells as claimed in claim 39, wherein the cell allocation device-providing step is performed so that the plate material has a third concavity in the first surface of the plate material for maintaining a second cell suspension pool in the third concavity, a fourth concavity in the second surface of the plate material, and a second plurality of longitudinal cutouts connected in parallel between the third and fourth concavities, and further comprising the steps of providing a second cell suspension containing cells to be cultured to said third concavity, and allowing the cells of the second cell suspension of the third concavity to precipitate into the second plurality of longitudinal cutouts by capillary action and then to the cell culture substrate, and to pool on the cell culture substrate at the fourth concavity.

41. A method for allocating cells as claimed in claim 40, wherein the first and second pluralities of longitudinal cutouts are provided in a parallel and alternating fashion in said plate material.

42. A method for allocating cells as claimed in claim 40, wherein the cell allocation device-providing step is performed so that the cell allocation device includes a masking plate operably engaged at a first surface thereof to the second surface of the plate material, said masking plate having a third plurality of longitudinal cutouts connected throughout from the first surface of the masking plate to a second surface of the masking plate so that the second and fourth concavities are isolatedly spaced from the cell culture substrate by the masking plate.

43. A method for allocating cells as claimed in claim 42, wherein the first, second and third pluralities of longitudinal cutouts are formed by photolithography.

44. A method for allocating cells as claimed in claim 40, wherein the first and second pluralities of longitudinal cutouts are formed by photolithography.

45. A cell allocation device for allocating cells on a culture substrate, comprising:
a plate material having first and second surfaces, a first concavity in the first surface of the plate material for maintaining a first cell suspension pool in the first concavity, a second concavity in the second surface of the plate material, and a first plurality of longitudinal cutouts connected in parallel between said first and second concavities, said first plurality of longitudinal cutouts having a construction such that cells in a cell suspension pass thereinto by capillary action when the second surface is in contact with the culture substrate.

46. A cell allocation device as claimed in claim 45, wherein the plate material has a third concavity in the first surface of the plate material for maintaining a second cell suspension pool in the third concavity, a fourth concavity in the second surface of the plate material, and a second plurality of longitudinal cutouts connected in parallel between the third and fourth concavities, said second plurality of longitudinal cutouts having a construction such that cells in a cell suspension pass thereinto by capillary action when the second surface is in contact with the culture substrate.

47. A cell allocation device as claimed in claim 46, wherein the first and second pluralities of longitudinal cutouts are provided in a parallel and alternating fashion in the plate material.

48. A cell allocation device as claimed in claim 46, further comprising a masking plate operably engaged at a first surface thereof to the second surface of the plate material, said masking plate having a third plurality of longitudinal cutouts connected throughout from the first surface of the masking plate to a second surface of the masking plate so that the second and fourth concavities are isolatedly spaced from the second surface of the masking plate.

* * * * *